Figure 1:
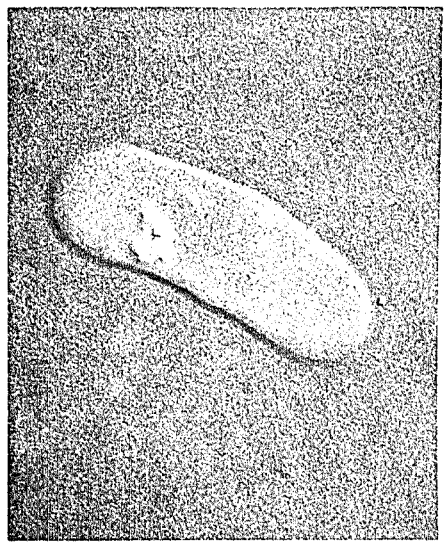

United States Patent [19]

Hashimoto et al.

[11] Patent Number: 4,645,667

[45] Date of Patent: Feb. 24, 1987

[54] ANTITUMOR AGENT AND PROCESS FOR MANUFACTURING SAID AGENT

[75] Inventors: Yoshiyuki Hashimoto, Sendai; Tomohiro Toida, Hachioji; Kazunori Sekine, Tokyo; Minoru Saito, Komae; Takuji Kawashima, Kawasaki; Morio Kuboyama, Tokyo, all of Japan

[73] Assignee: Morinaga Milk Industry Co., Ltd., Tokyo, Japan

[21] Appl. No.: 566,074

[22] Filed: Dec. 27, 1983

[30] Foreign Application Priority Data

Dec. 27, 1982 [JP] Japan ................... 57-226682

[51] Int. Cl.$^4$ ............ A61K 39/02; A61K 35/78
[52] U.S. Cl. ................... 424/92; 424/195.1
[58] Field of Search ................... 424/195, 92

[56] References Cited

PUBLICATIONS

Chem. Abst. 95:13097s, 1981.
Chem. Abst. 100:101626x, 1984.

*Primary Examiner*—Jerome D. Goldberg
*Assistant Examiner*—John W. Rollins, Jr.
*Attorney, Agent, or Firm*—Jordan and Hamburg

[57] ABSTRACT

This invention relates to an antitumor agent comprising as a main ingredient a chemically purified cell walls of microorganisms belonging to genus Bificobacterium having physical integrity of cell wall structure thereof, obtained without being subjected to chemical and/or physical destruction of said cell wall during removal of intracellular substances of said cell, and a process for manufacturing the same, which comprises the steps of; (a) treating said cells with surfactants, (b) treating said cells with proteases, nucleases, organic solvents and dilute acid, to remove intracellular substances out of said cells without destruction thereof, and (c) separating a chemically purified cell walls having physical integrity of cell wall structure thereof.

5 Claims, 3 Drawing Figures

1 μm

1 μm

1 μm

ANTITUMOR AGENT AND PROCESS FOR MANUFACTURING SAID AGENT

This invention relates to a substance having antitumor activity which comprises chemically purified cell walls obtained from microorganisms belonging to the well known genus Bifidobacterium (which will be hereinafter referred to as "bifidobacteria"), in an intact cell state without being subjected to a physical and/or chemical destruction of cells (the cells in an intact cell state will be hereinafter referred to as "intact cells") by removing only intracellular substances therefrom without disrupting the cell walls, and to a process for manufacturing the same.

TECHNICAL BACKGROUND AND PRIOR ART

Recently, it has been found that purified cell walls separated from microorganisms such a BCG (Bacillus Calmette-Guérin) or Nocardia, etc. have a host-mediated antitumor effect [Journal of National Cancer Institute, Volume 52, page 1571 (1974); Gann, Volume 69, page 19 (1978); Gann, Volume 67, page 669 (1976); Cancer Immunology and Immunotherapy, Volume 4, page 95 (1978)], and studies on manufacture of an antitumor agent from cell walls of other species have been made to separate purified cell walls of microorganisms having a higher antitumor activity and a clinical applicability. Particularly, gram-positive bacteria widely distributed in the natural world with no fear of existence of endotoxins have been regarded as very important, and purified cell walls having an antitumor effect have been obtained from some of gram-positive bacteria [Proceedings of the Japanese Cancer Association, the 40th Annual Meeting, page 107 (1981)].

Cell walls of gram-positive bacteria have an envelope-like structure based on a covalent bond of peptidoglycan with the so-called special structural substance which is specific to the species of bacteria in question and contains polysaccharides or teichoic acids as the main ingredient. The cell walls locate in contact with the outside of cell membrane to keep the shape of cells and act to protect the cytoplasm and its function from various external stimuli. Particularly, the peptidoglycan moiety is not only important as an active center of antitumor effect, but plays an important role also to keep the entire shapes of cell walls. That is, peptidoglycan is composed of reticular binding of glycan chains consisting of N-acetylglucoasamine and N-acetylmuramic acid with peptide chains in a three-dimensional structure and form a water-insoluble, physically very rigid macropolymers.

According to the conventional process for separating and extracting purified cell walls from bacteria, intracellular cytoplasmic ingredients were liberated and removed under specific conditions at first, and then crude cell walls remaining as water-insoluble residues were separated, and subjected to repeated purification treatment with enzymes such as protease and nuclease. Among these series of operations, particularly liberation and removal of intracellular cytoplasm ingredients were very important for increasing chemical purity of purified cell walls, and its specific procedures based on the species of bacteria have been widely studied.

That is, the studies are varied with the species of bacteria, including, for example, relatively easy occurrence of liberation of cytoplasmic ingredients only by changes in osmotic pressure as in vibrio costicolus as a gram-positive bacteria (Journal of General Microbiology, Volume 20, page 32 (1959)], or by treatment with a surfactant as in *Escherichia coli* [Journal of Bacteriology, Volume 136, page 723 (1978)], and only possible removal of cytoplasmic ingredients by disruption of cell walls by very vigorous physical treatment as in gram-positive coccus [Biken's Journal, Volume 2, page 143 (1959)], and such variety depends on physical and chemical properties of cell walls in the bacteria in question.

Generally, in the case of gram-positive bacteria, it is indispensable to disrupt cell walls by a physical means such as ultrasonic oscillation etc. or by a chemical means such as acids or cell wall-lytic enzymes, etc. owing to the said complicated ingredients and physically rigid cell walls, and such destructive treatment has been so far applied to many gram-positive bacteria as a common means for isolating purified cell walls of gram-positive bacteria. Thus, there has been no technical concept of extracting only purified cell walls from gram-positive bacteria without subjecting the cell walls to a physical and/or chemical destructive treatment.

However, according to the conventional process using the destructive treatment, not only cell walls are cut into finer fragments, resulting in considerable reduction in yield, but also non-specific breaking of the covalent bonds takes place on the peptidoglycan moiety and this leads to a very great disadvantage of lowering the antitumor effect from the bifidobacteria to improve the said conventional process, and have established the present invention.

The present invention provides an antitumor agent characterized by cell walls of intact cells of bifidobacteria, intracellular ingredients being removed from the cells without subjecting the cell walls to physical and chemical disruption, thereby leaving the cell walls, and also provides a process for preparing an antitumor agent, characterized by treating intact cells of bifidobacteria with a surfactant, and then treating the cells with proteases, nucleases, an organic solvents and a dilute acid, thereby removing intracellular ingredients from the cells and extracting the cell walls without disrupting the cell walls of the cells.

An object of the present invention is to provide a substance having antitumor activity comprising cell walls of cells of bifidobacteria and having a high activity.

Another object of the present invention is to provide a process for manufacturing a substance having antitumor activity having a high activity from bifidobacteria in high yield.

SPECIFIC DESCRIPTION OF THE INVENTION

The bifidobacteria for use in the present invention are the well known strains and are described in catalogs of American Type Culture Collection (which will be hereinafter referred to as ATCC), etc. and are readily available. Cells obtained by culturing these strains in the ordinary manner are used. It is desirable that the bofidobacteria are suspended in water or in a buffer solution, and heat-treated before the treatment with a surfactant. It is known that bacteria contain their own autolytic enzymes to degrade cell walls [K. Funazu and T. Tsuru: "Bacteriolytic Enzyme", page 14, published by Kodansha (1977)]. Thus, it is desirable to conduct heat treatment to inactivate the autolytic enzymes and protect the three-dimensional structure of cell walls. Desirable conditions for the heat treatment are such a short time as 60°–80° C. for 20–30 minutes or 10–15 minutes in boiling water to completely inactivate the autolytic enzymes and prevent denaturing of proteins by heating.

The surfactant for use in the present invention is any of commercially available neutral and anionic surfactants, and a neutral surfactant which can be more readily removed in a later step is preferable. For example, Triton X-100 or Tween 80 is preferable. The surfactant is used in an amount of 0.1–4% (w/v), preferably 0.2–1% (w/v).

Dried cells are suspended in a solution containing the surfactant in a ratio of 100 g of dried cells to 1.5–2 l of the solution containing the surfactant to extract the ingredients dissolved by the surfactant. Extracting temperature may be room temperature, and desirably 80°–90° C. for 30 minutes to one hour to enhance an extraction efficiency. To remove the surfactant remaining on the cells after the treatment with the surfactant, it is necessary to repeat centrifugal washing or filtration washing of the cells with distilled water, and a treatment with an organic solvent is desirable for increasing a washing efficiency. Used to this end are organic solvents that can be readily mixed with the surfactant and water such as alcoholic solvents, for example, methanol, ethanol, propanol, etc., and acetone, etc. The organic solvent is stirred together with the cells at room temperature for 12–24 hours to remove the remaining surfactant.

The protease for use in the present invention is a commercially available one, for example, trypsin, chymotrypsin, papain, pepsin, pronase (Kaken Kogaku K.K., Japan), etc. Protein digestion only by one kind of enzyme is not sufficient, and it is necessary to use several kinds of enzyme having different substrate specificity and optimum pH. According to a desirable mode, a protease having an optimum pH in the alkaline region (pH 7–8), such as trypsin, chymotrypsin, papain, etc. is used at first, and then an enzyme having an optimum pH in an acid region (pH 2–3), such as pepsin, etc. is used. Then, pronase having a low substrate specificity is further used.

That is, the cells treated with the surfactant is treated with trypsin, chymotrypsin or papain and ribonuclease and deoxyribonuclease as nucleases dissolved in 0.05M Tris-HCl buffer (pH 7.8) at 37° C. for 14–20 hours. Concentrations of enzymes for this purpose are 0.05–0.2% (w/v) for protease and 1/100–1/200 of the protease for ribnuclease and 1/1000–1/2000 of the protease for deoxyribonuclease.

Then, the treated cells are suspended in 0.01N HCl (pH 2) containing 0.05–0.2% (w/v) of pepsin and treated at 37° C. for 14–20 hours. Under a condition of pH 2–3, trypsin, chymotrypsin, papain, ribonuclease and deoxyribonuclease are inactivated, and further digested together with the intracellular protein by the pepsin. Then, the treated cells are treated by pronase dissolved in 0.05M Tris-HCl buffer (pH 7.4) at 37° C. for 14–20 hours. Desirable concentration of pronase for this purpose is 0.05–0.15% (w/v).

At pH 7–8, the existing pepsin is inactivated and digested together with the protein remaining in the cells by the pronase. At this stage, the protein other than the cell ingredients in the suspension is substantially only pronase, and the pronase is removed by thorough washing of cells, desirably by further dialysis.

Then, treatment with an organic solvent is conducted for defatting. Much water still remains on the cells, and thus fats are extracted at first with an alcoholic solvent such as methanol, ethanol, etc. or acetone, etc. which are completely miscible with water, then with a methanol-chloroform mixture or an acetone-chloroform mixture, etc., and finally with an organic solvent with a low polarity such as chloroform, hexane, etc. to complete the defatting operation.

Then, the treated cells are dried under reduced pressure to substantially constant weight, and then suspended again in 0.05M Tris-HCl buffer (pH 7.4), admixed with 0.05–0.15% (w/v) of pronase and treated at 37° C. for 14–20 hours.

Then, the treated cells are thoroughly washed to remove the pronase, and then suspended in 0.01N sulfuric acid, heat-treated in boiling water for 10–20 minutes, dialyzed against distilled water for 48–72 hours, and freeze-dried. The treatment with the dilute acid may be carried out between the treatment step with the protease and the treatment step with the organic solvent.

TEST 1

This test was conducted to investigate yield of the antitumor agent manufactured according the the present process.

(1) Preparation of samples:

(A) Sample 1 (antitumor agent manufactured according to the present process):

An antitumor agent manufactured from *Bifidobacterium infantis* ATCC 15697 in the manner as in Example 1 which follows.

(B) Sample 2 (antitumor agent manufactured according to the present process):

An antitumor agent manufactured from *Bifidobacterium longum* ATCC 15707 in the same manner as in Example 1 which follows.

(C) Sample 3 (antitumor agent manufactured according to the present process):

An antitumor agent manufactured form *Bifidobacterium longum* ATCC 15707 in the same manner as in Example 2, which follows.

(D) Sample 4 (antitumor agent manufactured according to the conventional process):

An antitumor agent manufactured in the following manner: A 100 g of freeze-dried cells of *Bifidobacterium infantis* ATCC 15697 was suspended in 1.2 l of distilled water, treated in an ultrasonic oscillator (Model 200M, made by Kubuta K.K., Japan) with a power of 200 W for 20 minutes to disrupt the cells, and then subjected to a low speed centrifuge (1,000 G for 30 minutes) to remove undisrupted cells as settled residues; the supernatant liquid was heat-treated at 60° C. for 30 minutes, and then subjected to a high speed centrifuge (20,000×G for 30 minutes), and the thus obtained residues were successively subjected to protein digestion treatment by trypsin and chymotrypsin, nucleic acid digestion treatment by ribonuclease and deoxyribonuclease, protein digestion treatment by pepsin, protein digestion treatment by pronase, organic solvent extraction by methanol and methanol-chloroform mixture and protein digestion treatment by pronase P under the same conditions as in Example 1.

(E) Sample 5 (antitumor agent manufactured according to the conventional process):

An antitumor agent manufactured in the following manner: A 80 g of freeze-dried cells of *Bifidobacterium longum* ATCC 15707 was suspended in 1.2 l of distilled water, and the suspension was placed in a ball mill containing 0.5 mm alumina balls (Universal Ball Mill UB-31, made by Yamato Kagaku K.K., Japan) and subjected to revolution at 50–60 rpm at 4° C. for 2 hours; cell disrupted products in the ball mill were washed out with the physiological salin and subjected twice to low speed centrifuge at 1,000×G for 30 minutes to remove undisrupted cells as residues; then the second centrifuge supernant liquid was heat-treated in boiling water for 10 minutes, and then subjected to high speed centrifuge (20,000×G for 30 minutes) to separate crude cell walls; the crude cell walls were subjected successively to protein digestion on treatment by papain, nucleic acid digestion treatment by ribonuclease and deoxyribonuclease, protein digestion treatment by pronase, organic solvent extraction by acetone, acetone-chloroform and hexane, and protein decomposition treatment by pronase under the same conditions as in Example 2.

(2) Test procedure

Samples 1–5 thus prepared were freeze-dried and then immediately weighed to calculate yields (%) on the basis of freeze-dried cells as starting materials. Preparation of said samples was repeated three times for one sample (Test Nos. I, II and III) to calculate the respective yields and also an average yield.

(3) Results

Test results are shown in Table 1.

TABLE 1

| Test No. | Yield (%) (the invention) | | | Yield (%) (conventional) | |
|---|---|---|---|---|---|
| | Sample 1 | Sample 2 | Sample 3 | Sample 4 | Sample 5 |
| I | 11.5 | 17.2 | 16.3 | 8.4 | 10.2 |
| II | 13.6 | 15.3 | 16.4 | 7.5 | 11.8 |
| III | 13.2 | 16.0 | 17.2 | 8.6 | 12.4 |
| Average | 12.77 | 16.17 | 16.63 | 8.17 | 11.47 |

As is obvious from Table 1, Sample 1 manufactured according to the present process could produce an antitumor agent in a yield 1.6 times as high as that of Sample 4 manufactured according to the conventional process, and Sample 3 manufactured according to the present process could do so in a yield 1.5 times as high as that of Sample 5 manufactured according to the conventional process.

On the other hand, Samples 2 and 3 manufactured from *Bifidobacterium longum* according to two different modes of the present process could obtain substantially equal yields. Thus, the present process can produce an antitumor agent in a substantially constant high yield without any substantial influence of kinds of surfactant, protease and organic solvent used.

TEST 2

This test was conducted to investigate chemical composition of the antitumor agent manufactured according to the present process.

(1) Test procedure (A) Method for analysis of neutral sugars: 50 mg each of the same Samples 1 and 4 as in the said Test 1 was separately weighed out, admixed with 5 ml of 1N sulfuric acid, and hydrolyzed at 100° C. for 6 hours. The respective hydrolyzate solutions were each desalted with Amberlite IRA-410 (carbonate form: $CO_2{}^{2-}$ form), then concentrated under reduced pressure, and made to 50.0 ml. A definite amount thereof was qualitatively and quantitatively determined in the conventional manner by gas-liquid chromatography.

(B) Method for analysis of amino acids and amino sugars: 50.0 mg each of the same Samples 1 and 4 as in the said Test 1 was separately weighed out, admixed with 5 ml of 6N-HCl and hydrolyzed at 105° C. for 14 hours. The respective hydrolyzate solutions were each evaporated to dryness in a rotary evaporator to remove HCl and then made to 50.0 ml. A definite amount thereof was qualitatively and quantitatively determined in the conventional manner by an amino acid automatic analyzer.

(2) Results:

Compositions and contents of neutral sugars, amino acids and amino sugars of Samples 1 and 4 are shown in Table 2.

TABLE 2

| Composition | Sample 1 | | Sample 4 | |
|---|---|---|---|---|
| | mg/g | μM/g | mg/g | μM/g |
| Neutral sugar (Total) | 615 | — | 685 | — |
| (Component sugar) | | | | |
| Galactose | 446 | 2478 | 507 | 2817 |
| Glucose | 169 | 939 | 178 | 989 |
| Amino acid (total) | 154.30 | — | 125.38 | — |
| (Component amino acid) | | | | |
| Alanine | 53.30 | 598.3 | 45.85 | 515.1 |
| Glutamic acid | 22.40 | 152.2 | 19.74 | 134.2 |
| Threonine | 18.04 | 151.4 | 16.80 | 141.1 |
| Serine | 19.29 | 183.6 | 18.04 | 171.8 |
| Ornithine | 22.16 | 167.7 | 17.02 | 128.8 |
| Lysine | 1.27 | 8.7 | 1.50 | 10.2 |
| Glycine | 1.83 | 12.4 | 0.95 | 12.6 |
| Aspartic acid | 11.25 | 8.5 | 0.69 | 5.2 |
| Proline | 0 | — | 0 | — |
| Valine | 0.74 | 6.3 | 1.83 | 15.60 |
| Cystine | 0 | — | 0.77 | 3.20 |
| Methionine | 0.61 | 4.0 | 0 | — |
| Leucine | 1.68 | 12.8 | 1.34 | 10.20 |
| Isoleucine | 1.56 | 11.9 | 0.85 | 6.44 |
| Tyrosine | 1.17 | 6.5 | 0 | — |
| Phenylalanine | 0 | — | 0 | — |
| Histidine | 0 | — | 0 | — |
| Arginine | 0 | — | 0 | — |
| Amino sugar (total) | 51.84 | — | 73.79 | — |
| (Component amino sugar) | | | | |
| Glucosamine | 20.40 | 113.88 | 32.64 | 182.20 |
| Muramic acid | 31.44 | 125.26 | 41.15 | 164.0 |

As is obvious from Table 2, Sample 1 manufactured according to the present process consists of 61.5% of neutral sugars, 15.4% of amino acids and 5.2% of amino sugars. Sample 4 manufactured according to the conventional process also has a similar composition and consists of 68.5% of neutral sugars, 12.5% of amino acids and 7.4% of amino sugars. In the amino acid composition, both Samples have such an amino acid molar ratio as alanine: glutamic acid: threonine: serine: ornithine=4:1:1:1:1, including substantially no other amino acids. In the neutral sugars, both Samples also contain glucose and galactose in a molar ratio of 1:2.6–2.8. In the amino sugars, glucosamine and muramic acid are contained also in a substantially equimolar ratio.

The foregoing results of analysis show that the antitumor agent manufactured according to the present process has a chemical uniformity equivalent to that of the antitumor agent manufactured according to the conventional process. Particularly, amino acids contained in all of the proteins, such as phenylalanine, arginine, thyrosine, etc., are substantially not detected. This menas that the intracellular proteins are substantially completely removed according to the present process.

TEST 3

This test was conducted to confirm that the antitumor agent manufactured according to the present process contians undisrupted cell walls of bifidobacteria.

(1) Test procedure 110 mg each of the same Samples 1 and 4 as in the said Test 1 was uniformly suspended separately in 10 ml of distilled water, admixed with an equal amount of 2.5% (V/V) glutaraldehyde solution, thoroughly stirred, and left standing at room temperature for 12 hours. The suspension was centrifugally washed three times with distilled water (6,000×G for 20 minutes) and dialyzed agianst 5 l of distilled water for 48 hours. The dialysis syspension were subjected to centrifuge (6,000×G for 20 minutes). The sediments were admixed with 40 ml of methanol, throughly stirred and prepared into a sample for electron microscope observation in the ordinary manner. As a control, intact cells of *Bifidobacterium infantis* ATCC 15697 were treated in the same manner as described above.

(2) Results

Figure 2:
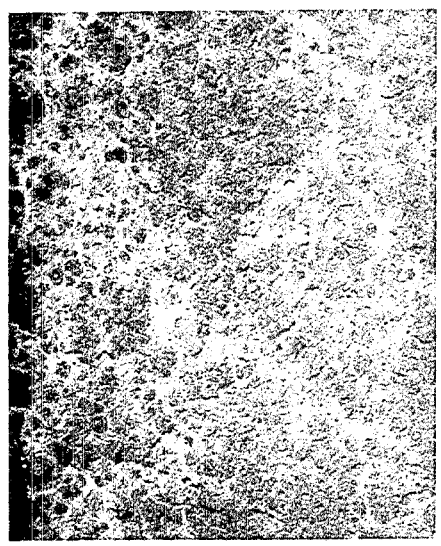
Figure 3:
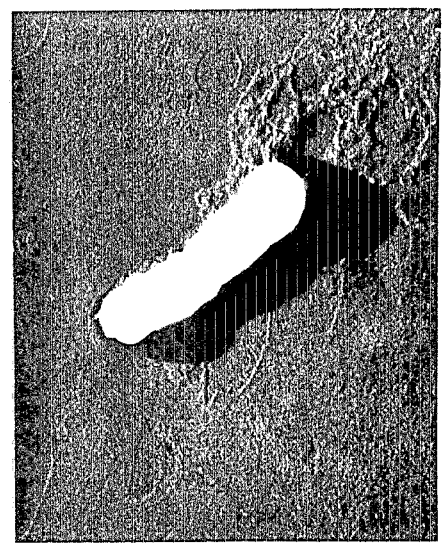

FIGS. 1, 2 and 3 are electron micrographs of Samples 1 and 4, and control by shadowing (magnification: ×25,000). It is obvious from FIG. 2 that the antitumor agent prepared according to the conventional process the cell walls are completely disrupted into pieces and are indefinite in shapes, where as it is shown in FIG. 1 that the antitumor agent manufactured according to the present process the envelope-like three-dimensional structure is retained, and the shapes of intact cells remain as they are.

Thus, the antitumor agent manufactured according to the present process is not only chmically uniform, but is quite different from that manufactured according to the conventional process also in the shapes observed by an electron microscope.

The electron micrograph of untreated bifidobacteria (control) of FIG. 3 shows that the cells are displayed as white, and this means existence of intracellular ingredients (cytoplasm) in the cells.

TEST 4

This test was conducted to compare the antitumor effect of the antitumor agent manufactured according to the present process with that manufactured according to the conventional process.

(1) Test procedure

BALB/C male mice (age: 7 weeks, body weight: 22±2 g) were used as test animals. A syngeneic tumor cells of BALB/C mice, Meth—A fibrosarcoma (Sloan—Kettering Institute of Cancer Research, New York), was prepared to be $1.0 \times 10^6$ viable cells/cc in the ordinary manner, 0.1 cc of which was subcutaneously inoculated into the flank of the mice. Diameter of tumor was measured by a caliper 4 days after the inoculation, and mice were distributed into administration groups so that each group can have a definite average diameter of tumor. Five days after the incocualtion 0.1 cc of a suspension of Sample 1 or 4 in a 5% mannitol solution at a concentration of 1.0 mg/cc was administered into the tumor-growing site 5 times on every other day. To the control animals, 0.1 cc of 5% mannitol was administered. The reason why 5% mannitol solution was used as a dispersion medium is to uniformly distribute the sample, and the solution itself has the same osmotic pressure as that of the body fluid (286 Osm/kg) and has no influence on the growth of tumor at all.

The effect was determined by investigating the number of mice with complete regression of tumor in each administration group and calculating a tumor regression ratio according to Tumor Regression Test [Journal of National Cancer Institute Monograph, Volume 39, page 115 (1973)].

(3) Results

Test results are shown in Table 3.

TABLE 3

| Administration group | Dosage per mouse (μg × 5) | Number of tested mice | Number of mice with complete tumor regression | Tumor regression ratio (%) | P value* |
|---|---|---|---|---|---|
| Control | — | 40 | 0 | 0 | — |
| Sample 1 | 100 | 20 | 14 | 70 | $4.5 \times 10^{-9}$ |
| Sample 4 | 100 | 20 | 4 | 20 | 0.02 |

*Fischer's test

As is obvious from Table 3, no complete tumor regression was observed in the group of 5% mannitol administration as the control, whereas complete tumor regression was observed at four mice among 20 mice of the group of Sample 4 administration. On the other hand, the tumor regression ratio was much increased in the group of Sample 1 administration, where complete tumor regression was observed at 14 mice among 20 mice, and had a statistically high significance ($P=4.5\times10^{-9}$), as compared with the control.

A significant difference ($P=3.6\times10^{-3}$) was also observed in comparison of the group of Sample 1 administration with the group of Sample 4 administration.

Thus, it was found that the antitumor agent manufactured according to the present process had a stronger antitumor effect than the antitumor agent manufactured according to the conventional process.

TEST 5

This test was conducted to determine a minimum effective dosage of the antitumor agent manufactured according to the present process.

(1) Test procedure

Determination of a minimum effective dosage of an antitumor agent was conducted according to said Ribi et al's Tumor Suppression Test.

A suspension of Meth-A tumor cells at $1.0\times10^6$ viable cells/cc prepared in the conventional manner, and a suspension containing 1.0 mg/cc, 0.5 mg/cc, 0.25mg/cc, 0.20 mg/cc or 0.1 mg/cc of Sample 1 in 5% mannitol solution were mixed in equal amounts under a sterile condition, and 0.2 cc of the mixture was subcutaneously administered into the flank of BALB/C made mice (age: 7 weeks, body weight: 22±1 g). As a control, 0.2 cc of a mixture of 5% mannitol and the said tumor suspension was administered. 4 weeks after the administration, the mice was inspected to determine generation of tumor.

(2) Results

Test results are shown in Table 4.

TABLE 4

| Administration group | Dosage per mouse (μg) | Number of tested mice | Number of tumor-suppressed mice | Tumor suppression ratio (%) | P value* |
|---|---|---|---|---|---|
| Control | — | 20 | 0 | 0 | — |
| Sample 1 | 100 | 20 | 20 | 100 | $1.5 \times 10^{-11}$ |
|  | 50 | 20 | 17 | 85 | $2.6 \times 10^{-8}$ |
|  | 25 | 20 | 14 | 70 | $3.3 \times 10^{-6}$ |
|  | 20 | 20 | 7 | 35 | 0.008 |
|  | 10 | 20 | 0 | 0 | 1.00 |

*Fischer's test

As is obvious from Table 4, tumor generation was completely suppressed in the group of 100 μg/mouse dosage in the group of Sample 1 administration, and 85% suppressed in the group of 50 μg/mouse dosage. Furthermore, a remarkable effect (suppression ratio: 70%) was observed also in the group of 25 μg/mouse dosage. On the other hand, in the group of 20 μg/mouse dosage, the effect was considerably reduced, and the suppression ratio was 35%. Thus, it was found that the antitumor agent manufactured according to the present process had a remarkable effect at a dosage of 25 μg/mouse, and had a very strong antitumor effect.

TEST 6

This test was conducted to investigate the toxicity of the antitumor agent manufactured according to the present process.

(1) Test procedure

A/J male and female mice (age: 7 weeks, body weight: 22±2 g) were used as test animals. A suspension of Sample 1 in 5% mannitol solution was administered into the abdominal cavity at dosages of 5 mg, 10 mg, and 50 mg per kilogram of body weight every day for 10 days. As a control, a 5% mannitol solution was administered every day for 10 days. One group consisted of 10 mice, and groups were observed for one month after the administration to investigate the number of dead mice.

(2) Results

Test results are shown in Table 5.

TABLE 5

| Administration Group | Dosage (mg/kg × 10) | Sex | Number of tested mice | Number of dead mice | Mortality (%) |
| --- | --- | --- | --- | --- | --- |
| Control | — | ♂ | 10 | 10 | 0 |
|  | — | ♀ | 10 | 0 | 0 |
| Sample 1 | 5 | ♂ | 10 | 0 | 0 |
|  | 5 | ♀ | 10 | 0 | 0 |
|  | 10 | ♂ | 10 | 0 | 0 |
|  | 10 | ♀ | 10 | 0 | 0 |
|  | 50 | ♂ | 10 | 0 | 0 |
|  | 50 | ♀ | 10 | 0 | 0 |

As is obvious from Table 5, no mice were dead at every dosage of Sample 1, and no anaphylaxis, a kind of acute toxicity observed at continued administration of an antigenic substance, was observed. The foregoing results show that the antitumor agent manufactured according to the present process has a much less toxicity.

EXAMPLE 1

A 100 g of freeze-dried cells of *Bifidobacterium infantis* ATCC 15697 obtained by culturing in the ordinary manner was suspended in 1.5 l of the physiological saline, heated in boiling water for 15 minutes, cooled, once centrifugally washed with the physiological saline (6,600×G for 20 minutes), then resuspended in 1.5 l of the physiological saline, and stirred at 4° C. for 20 hours. Then, the suspension was centrifugally washed three times with distilled water (6,600×G for 20 minutes), suspended in 700 ml of distilled water, admixed with an equal amount of HEPES (N-2-hydroxy-ethylpyperazine-N-2-ethanesulfonic acid) buffer solution (pH 7.0) containing 1% (V/V) Triton X-100 (made by Sigma Co.) and subjected to extraction at 80°–90° C. with stirring. Then, the suspension was centrifugally washed three times with distilled water (6,600×G for 30 minutes), and suspended in 2 l of distilled water, stirred at 4° C. for 24 hours, and centrifugally washed three times with distilled water (6,600×G for 20 minutes). Then, the residues were admixed with 1.6 l of methanol, stirred at room temperature for 16 hours, and filtered. The cakes on the filter were thoroughly washed with methanol, and then with distilled water, and then suspended in 1.6 of 20 mM $CaCl_2$-0.05M Tris-HCl buffer (pH 7.8) containing 0.05% (W/V) of trypsin (made by Sigma Co.), 0.05% (W/V) of chymotrypsin (made by Sigma Co.), 20 mg of ribonuclease (made by Sigma Co.) and 1 mg of deoxyribonuclease (made by Sigma Co.), dropwise admixed with 0.2 ml of toluene as an antiseptic, and subjected to enzyme treatment at 37° C. for 20 hours.

Then, the thus treated cells were centrifugally washed four times with distilled water and then twice with 0.01N-HCl (6,600×G for 40 minutes), suspended in 800 ml of 0.01N-HCl containing 0.1% (W/V) of pepsin (Made by ICN Pharmaceuticals) and treated at 37° C. for 20 hours. Then, the suspension was centrifugally washed four times with distilled water (20,000×G for 30 minutes), suspended in 800 ml of 20 mM $CaCl_2$-0.05M Tris-HCl buffer (pH 7.4) containing 0.1% (W/V) of Pronase P (made by Kaken Kagaku K.K., Japan), admixed with ethanol as an antiseptic at an ultimate concentration of 3% (V/V), and treated at 37° C. for 20 hours.

Then, the suspension was centrifugally washed with distilled water (20,000×G for 30 minutes), and the sediments were admixed with 1.6 l of methanol and refluxed for 4 hours. Then, the suspension was filtered, and the cakes on the filter were washed three times with methanol, and resuspended in 700 ml of methanol, admixed with an equal amount of chloroform, thoroughly mixed and then refluxed for 4 hours. Then, the residues were suspended in 1.4 l of chloroform and refluxed for 4 hours. After the extraction with the organic solvent, the thus treated cells were separated by filtration and dried under reduced pressure. Then the dried cells were suspended in 600 ml of 20 mM $CaCl_2$-0.05M Tris-HCl buffer (pH 7.4) containing 0.05% (W/V) of Pronase P, admixed with ethanol to make 3% (V/V), and treated at 37° C. for 20 hours. These operations were repeated twice, and the suspension was centrifugally washed repeatedly with distilled water (20,000×G for 30 minutes). The residues were suspended in 500 ml of 0.01N-$H_2SO_4$ and treated in boiling water for 20 minutes. Then, the suspension was centrifuged (20,000×G for 30 minutes) and the residues were centrifugally washed three times with distilled water, and the sediments were dialyzed against 10 l of distilled water for 72 hours. The dialysis residues were freeze-dried, whereby about 12 g of powdery antitumor agent was obtained.

EXAMPLE 2

A 80 g of freeze-dried cells of *Bifidobacterium longum* ATCC 15707 obtained by culturing in the ordinary manner was suspended in 1.2 l of the physiological saline, heat-treated at 80° C. for 30 minutes, centrifugally washed once with the physiological saline and then three times with distilled water (6,600×G for 20 minutes), then suspended in 10 mM $MgCl_2$ solution, and stirred at 4° C. for 20 hours. Then, the suspension was centrifugally washed four times with distilled water (6,600×G for 20 minutes), and the sediments were admixed with 1 l of HEPES buffer (pH 7.0) containing 0.2% (V/V) of sodium dodecylsulfate (made by Wako Pure Chemical Industries, Ltd., Japan) and subjected to extraction at room temperature for one hour with stirring. Then, the suspension was centrifuged (6,600×G for 30 minutes) and the sediments were washed four times with distilled water and then dialyzed against distilled water for 72 hours. The dialysis residues were centrifuged (6,600×G for 30 minutes), and the sediments were admixed with 1.2 l of propanol and stirred at room temperature for 24 hours. Then, the suspension was filtered, and the residues were washed successively with propanol, methanol and water, then admixed with 0.067M phosphate buffer (pH 7.2) containing 0.1% (W/V) of papain (made by Sigma Co.), and treated at 37° C. for 6 hours. Then, the thus treated cells were separated by centrifuge (6,600 G for 30 minutes), thoroughly washed, then suspended in 10 mM magnesium acetate solution containing 15 mg of ribonuclease and 800 μg of deoxyribonuclease, and treated at 37° C. for 18 hours. Then, the thus treated cells were separated by filtration, thoroughly washed with distilled water with stirring on the filter, and further likewise with 0.01N-HCl, suspended in 1 l of 0.01N-HCl containing 0.1% (W/V) of pepsin (made by ICN Pharmaceuticals), and treated at 37° C. for 20 hours. Then, the thus treated cells were separated by filtration, thoroughly washed with 0.05M Tris-HCl buffer (pH 7.4) on the filter, suspended in 1 l of 20 mM $CaCl_2$-Tris-HCl buffer (pH 7.4) containing 0.1% (W/V) of pronase P (made by Kaken Kagaku K.K., Japan), admixed with ethanol at an ultimate concentration of 3% (V/V), and treated at 37° C. for 20 hours.

Then, the suspension was filtered, and the residues were thoroughly washed with distilled water, suspended in 600 ml of 0.01N-$H_2SO_4$, and treated in boiling water for 20 minutes. The thus treated cells were separated by filtration, thoroughly washed, and dialyzed at 4° C. for 48 hours, and the dialysis residues were centrifuged (20,000×G for 30 minutes). The sediments were admixed with 1 l of acetone, refluxed for 4 hours, further, refluxed with 1 l of acetone-chloroform (1:1 by V/V) and then with 1 l of n-hexane for 4 hours, and dried under reduced pressure.

Then, the thus treated cells were suspended in 500 ml of 20 mM $CaCl_2$-0.05M Tris-HCl buffer (pH 7.4) containing 0.05% (W/V) of pronase P, admixed with ethanol to make 3% (V/V), and treated at 37° C. for 20 hours. These operations were further repeated twice, and then the suspension was centrifugally washed repeatedly with distilled water (20,000×G for 30 minutes), and dialyzed against distilled water for 72 hours. The dialysis residues were freeze-dried, whereby about 13 g of powdery antitumor agent was obtained.

EFFECT OF THE INVENTION

The effects obtained by the present invention are as follows:

(1) An antitumor agent can be manufactured from the bifidobacteria in a higher yield than in the conventional process.

(2) A chemically uniform antitumor agent can be obtained.

(3) Purified cell walls with a complete three-dimensional structure can be obtained and an antitumor agent with a constant quality can be obtained because there is no disruption of cell walls of the bifidobacteria.

(4) An antitumor agent with a strong antitumor effect can be obtained.

What is claimed is:

1. A process for preparing a substance having antitumor activity comprising the steps of;
 (a) Culturing microorganisms selected from the group consisting of *Bifidobacterium infantis, Bifidobacterium longum* and mixtures thereof in a conventional medium for bididobacteria until a sufficient number of cells are obtained, and separating cells of said microorganisms from said medium,
 (b) heating said cells, suspended in a physiological saline solution, at 60° to 100° C. for 10 to 30 minutes, and separating said cells from said suspension in physiological saline solution,
 (c) suspending said separated cells of step (b) in 4-(2-hydroxethyl)-1-piperazineethanesulfonic acid buffer solution of about neutral pH containing 0.1 to 0.4% (w/v) of a surface active agent selected from the group consisting of polyethylene glycol p-isooctylphenyl ether, polyoxyethylene (20) Sorbitan mono-oleate, sodium dodecylsulfate and mixtures thereof, in a ratio of 15 to 20 ml per gram of said cells, maintaining said solution at 80° to 90° C. for 30 to 60 minutes to remove cellular substances, and separating said cells from said suspension in said buffer solution,
 (d) suspending said separated cells of step (c) in a hydrophilic organic solvent selected from the group consisting of methanol, ethanol, propanol, acetone and mixtures thereof, at room temperature for 12 to 24 hours to remove said surface active agent, and separating said cells from said suspension in said organic solvent,
 (e) suspending said separated cells of step (d) in 2-amino-hydroxymethyl-1,3-propanediol or phosphate buffer solution of about neutral pH containing 0.05 to 0.2% (w/v) protease selected from the group consisting of trypsin, chymotrypsin, papain and mixtures thereof and ribonuclease in a concentration of 1/100 to 1/200 of said protease and deoxyribonuclease in a concentration of 1/1000 to 1/2000 of said protease, hydrolizing the cellular protein and nucleic acid at about 37° C. for 14 to 24 hours, and separating said cells from said suspension in the last said buffer solution,
 (f) suspending said separated cells of step (e) in 0.01N HCl of pH 2 to 3 containing 0.05 to 0.2% (w/v) of pepsin, hydrolyzing the cellular protein at about 37° C. for 14 to 24 hours, and separating said cells from said suspension in said 0.01N HCl solution,
 (g) suspending said separated cells of step (f) in 2-amino-hydroxymethyl-1,3-propanediol or phosphate buffer solution of about neutral pH containing 0.05 to 0.2% (w/v) of pronase, hydrolyzing the proteinous substances at about 37° C. for 14 to 24 hours, and separating said cells from said suspension in the last said buffer solution,
 (h) removing cellular lipids from said separated cells of step (g) with an organic solvent selected from the group consisting of methanol, ethanol, acetone and mixtures thereof, with a methanol-chloroform mixture or an acetone-chloroform mixture, and then with hexane or chloroform in sequence,
 (i) suspending said cells from which the lipids were substantially removed in a 2-amino-hydroxymethyl-1,3-propanediol or phosphate buffer solution of about neutral pH containing 0.05 to 0.14% (w/v) of pronase, hydrolyzing the proteinous substances at about 37° C. for 14 to 24 hours, and separating said cells from said suspension in the last said buffer solution, (j) suspending said separated cells from step (i) in a diluted sulfuric acid solution, heating from 10 to 20 minutes in boiling water, and separating said cells from said suspension in said diluted sulfuric acid solution, (k) dialyzing said cells of step (j) using distilled water for 48 to 72 hours, and (l) freeze-drying said dialyzed cells whereby cell walls having physical structural integrity without intracellular substances are obtained.

2. A process according to claim 1, wherein said heating in step (b) occurs at 60° to 80° C. for 20 to 30 minutes.

3. A process according to claim 1, wherein said heating in step (b) occurs in boiling water for about 10 to 15 minutes.

4. An antitumor agent made according to the process of claim 1.

5. A process for preparing a substance having antitumor activity comprising the steps of;

(a) culturing microorganisms selected from the group consisting of *Bifodobacterium infantis, Bifidobacterium longun,* and mixtures thereof in a conventional medium for bifidobacteria, and separating cells of said microorganisms from said medium, (b) heating said cells, suspended in a physiological saline solution, at 60° to 100° C. for 10 to 30 minutes, and separating said cells from said suspension in physiological saline solution.

(c) suspending said separated cells of step (b) in 4-(2-hydroxethyl)-1-piperazineethanesulfonic acid buffer solution of about neutral pH containing 0.1 to 0.4% (w/v) of a surface active agent selected from the group consisting of polyethylene glycol p-isooctylphenyl ether, polyoxyethylene (20) sorbitan mono-oleate, sodium dodecylsulfate and mixtures thereof, in a ratio of 15 to 20 ml per gram of said cells, maintaining said solution at 80° to 90° C. for 30 to 60 minutes to remove cellular substances, and separating said cells from said suspension in said buffer solution, (d) suspending said separated cells of step (c) in a hydrophilic organic solvent selected from the group consisting of methanol, ethanol, propanol, acetone and mixtures thereof, at room temperature for 12 to 24 hours to remove said surface active agent, and separating said cells from said suspension in said organic solvent, (e) suspending said separated cells of step (d) in 2-amino-hydroxymethyl -1,3-propanediol or phosphate buffer solution of about neutral pH containing 0.05 to 0.2% (w/v) protease selected from the group consisting of trypsin, chymotrypsin, papain and mixtures thereof and ribonuclease in a concentration of 1/100 to 1/200 of said protease and deoxyribonuclease in a concentration of 1/1000 to 1/2000 of said protease, hydrolizing the cellular protein and nucleic acid at about 37° C. for 14 to 24 hours, and separating said cells from said suspension in the last said buffer solution, (f) suspending said separated cells of step (e) in 0.01N HCl of pH 2 to 3 containing 0.05 to 0.2% (w/v) of pepsin, hydrolyzing the cellular protein at about 37° C. for 14 to 24 hours, and separating said cells from said suspension in said 0.01N HCl solution, (g) suspending said separated cells of step (f) in 2-amino-hydroxymethyl -1,3-propanediol or phosphate buffer solution of about neutral pH containing 0.05 to 0.2% (w/v) of pronase, hydrolyzing the proteinous substances at about 37° C. for 14 to 24 hours, and separating said cells from said suspension in the last said buffer solution, (h) suspending said separated cells from step (g) in a diluted sulfuric acid solution, heating from 10 to 20 minutes in boiling water, and separating said cells from said suspension in said diluted sulfuric acid solution, (i) removing cellular lipids from said separated cells of step (h) with an organic solvent selected from the group consisting of methanol, ethanol, acetone and mixtures thereof, with a methanol-chloroform mixture or an acetone-chloroform mixture, and then hexane or chloroform in sequence, (j) suspending said cells from which the lipids were substantially removed in 2-amino-hydroxymethyl -1,3-propanediol buffer solution of about neutral pH containing 0.05 to 0.14% (w/v) of pronase, hydrolyzing the proteinous substances at about 37° C. for 14 to 24 hours, and separating said cells from said suspension in the last said buffer solution, (k) dialyzing said cells of step (j) using distilled water for 48 to 72 hours, and (l) freeze-drying said dialyzed cells whereby cell walls having physical structural integrity without intracellular substances are obtained.

* * * * *